United States Patent [19]
Mizushima et al.

[11] Patent Number: 5,869,532
[45] Date of Patent: Feb. 9, 1999

[54] TAURINE DERIVATIVES FOR USE IN CLEANSER COMPOSITIONS

[75] Inventors: Hiromoto Mizushima; Masakatsu Takahashi, both of Wakayama; Hiroe Tanahashi, Tokyo; Takashi Matsuo, Ichikawa, all of Japan

[73] Assignee: Kao Corporation, Tokyo, Japan

[21] Appl. No.: 693,252

[22] PCT Filed: Feb. 20, 1995

[86] PCT No.: PCT/JP95/00242

§ 371 Date: Aug. 19, 1996

§ 102(e) Date: Aug. 19, 1996

[87] PCT Pub. No.: WO95/22522

PCT Pub. Date: Aug. 24, 1995

[30] Foreign Application Priority Data

Feb. 22, 1994 [JP] Japan ..................................... 6/24443

[51] Int. Cl.⁶ .......................... A61K 7/035; C07C 309/69
[52] U.S. Cl. .......................... 514/625; 514/627; 514/629; 558/49; 424/69; 424/70; 510/131; 510/133
[58] Field of Search ............................... 558/49; 514/627, 514/629, 625; 510/127, 131, 133

[56] References Cited

U.S. PATENT DOCUMENTS 5,328,630   7/1994   Nozaki et al. ........................... 252/117

OTHER PUBLICATIONS

Butskus et al., J. Gen. Chem. USSR, 30(4), 1799–1800, 1960.
Chem. Abstracts, 87(22), abstract no. 169551n, p. 84, Mar. 6, 1978.
Chem. Abstracts, 111(20), abstract no. 180445r, p. 404, Nov. 13, 1989.

*Primary Examiner*—Johann Richter
*Assistant Examiner*—Laura R. C. Lutz
*Attorney, Agent, or Firm*—Oblon, Spivak, McClelland, Maier & Neustadt, P.C.

[57] ABSTRACT

Taurine derivatives represented by the following formula (1) and cleanser compositions containing the same:

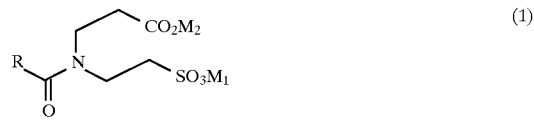

wherein R is a linear or branched alkyl or alkenyl group having 5 to 21 carbon atoms, and $M_1$ and $M_2$ are the same or different from each other and each independently is a hydrogen atom, an alkali metal atom, ½ (an alkaline earth metal atom), an ammonium group, etc.,
are excellent in foaming, detergency, comfort in use, rinsability, safety and biodegradability and are employed as a cleanser for the hair and body or tableware.

15 Claims, No Drawings

TAURINE DERIVATIVES FOR USE IN CLEANSER COMPOSITIONS

This application is a 371 of PCT/JP95/00242 filed Feb. 20, 1995.

BACKGROUND OF THE INVENTION

1. Field of the Invention

The present invention relates to novel taurine derivatives, processes for producing the same, and cleanser compositions containing such taurine derivatives. Moreover, the present invention relates to other taurine derivatives which are useful as intermediates for synthesizing the above-mentioned taurine derivatives and are themselves useful as cleansers, a process for producing the same, and cleanser compositions containing such taurine derivatives. The present invention also relates to methods of washing hair or skin using such taurine deirvatives.

2. Discussion of the Background

In recent years, it has become demanded that the surfactants used as cleansers have excellent properties such as biodegradability, safety toward the skin, eyes and hair, foaming power, comfort in the use thereof, and rinsability as well as surface activity. Acylated amino acid surfactants, imidazoline surfactants, alkyl phosphate salts, saccharide surfactants such as alkyl glycosides have become widely employed as surfactants meeting the above demand.

Generally, these surfactants are costly and unsatisfactory in foaming power and detergency which are particularly important in the use as a cleanser, while they are excellent in other properties such as safety. Therefore, it is rare that these surfactants per se are independently used as the main ingredient of a cleanser such as a body cleanser and a shampoo. These surfactants are generally used together with a conventional anionic surfactant such as an alkyl sulfate, an alkyl ether sulfate and a fatty acid soap. Therefore, the development of a cleanser which is available at a low cost, is excellent in foaming power, detergency and comfort in the use thereof, and ensures high safety, is strongly demanded in the art.

SUMMARY OF THE INVENTION

Accordingly, it is one object of the present invention to provide novel surfactants.

It is another object of the present invention to provide surfactants with excellent biodegradability, safety toward the skin, eyes and hair, comfort in use, foaming power, rinsability and surface activity.

It is another object of the present invention to provide novel processes for producing such surfactants.

It is another object of the present invention to provide novel intermediates for preparing such surfactants.

It is another object of the present invention to provide novel compositions which contain such surfactants.

It is another object of the present invention to provide novel methods of washing hair or skin with such compositions.

It is another object of the present invention to provide novel methods of washing hair or skin with such surfactants.

These and other objects, which will become apparent during the following detailed description, have been achieved by the inventors' discovery that amide anionic surfactants having a sulfonic acid group and a carboxyl group as ionic groups and which are derived from taurine are excellent in foaming, detergency, comfort in use, rinsability, safety and biodegradability.

Thus, the present invention provides a taurine derivative represented by the following formula (1) which is available at a low cost, is excellent in foaming power, detergency and comfort in the use thereof, and ensures high safety, and also a process for producing the same:

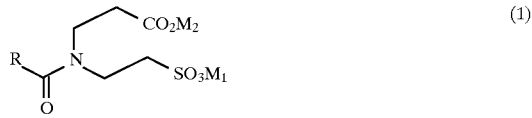
(1)

wherein R is a linear or branched alkyl or alkenyl group having 5 to 21 carbon atoms, and $M_1$ and $M_2$ are the same or different from each other and each independently is a hydrogen atom, an alkali metal atom, ½ (an alkaline earth metal atom), an ammonium group, a mono-, di-, tri- or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid.

Further, the present invention provides taurine derivatives represented by the following formulae (4), (5) and (6), and processes for producing them:

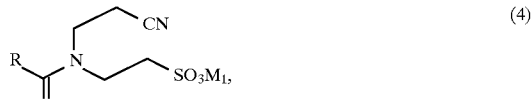
(4)

(5)

(6)

wherein R, $M_1$ and $M_2$ are each as defined above.

The taurine derivatives represented by the above formulae (4), (5) and (6) are useful as intermediates for producing the taurine derivatives represented by the above formula (1).

Furthermore, the present invention provides a cleanser composition comprising the taurine derivative represented by the above formulae (1) or (4).

In addition, the present invention provides a method of washing hair or skin which comprises contacting said hair or skin with a composition comprising a taurine derivative represented by the above formulae (1) or (4), and a method of washing hair or skin which comprises using a taurine derivative represented by the above formula (1).

There has been known that acylmethyltaurine [RCON($CH_3$)($CH_2$)$_2$$SO_3$Na, wherein R is, e.g., a group represented by the formula: $CH_3(CH_2)_{10}$—] can be used as a cleanser for the head skin and hair [see Kiyoshi Miyazawa, et. al., Yukagaku (Oil Chemistry), Vol.38, No.4, p.297 (1989)]. However, the chemical structures of the taurine derivatives according to the present invention are different from that of the above acylmethyltaurine.

DETAILED DESCRIPTION OF THE PREFERRED EMBODIMENTS

In the formulae (1) and (4), R is a linear or branched alkyl or alkenyl group having 5 to 21 carbon atoms, preferably 7 to 19 carbon atoms, still more preferably 9 to 13 carbon atoms. Specific examples of the above alkyl and alkenyl groups include the n-pentyl group, n-heptyl group, n-nonyl group, n-undecyl group, n-tridecyl group, n-pentadecyl group, n-heptadecyl group, methylhexadecyl group and heptadecenyl group. Of these, the n-nonyl group, n-undecyl group and n-tridecyl group are preferred.

In the formulae (1), (4), (5) and (6), $M_1$ and $M_2$ are the same or different from each other and each independently is a hydrogen atom, an alkali metal atom, ½ (an alkaline earth metal atom), an ammonium group, a mono-, di-, tri- or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid (glutamine, arginine, histidine or lysine). Of these, a hydrogen atom, a sodium atom, a potassium atom, an ammonium group, a triethanolammonium group, a diethanolammonium group and a monoethanolammonium group are preferred, and a hydrogen atom, a sodium atom, a potassium atom and an ammonium group are especially preferred.

The following compounds and their salts are preferred among the taurine derivatives of the present invention represented by the above formula (1).

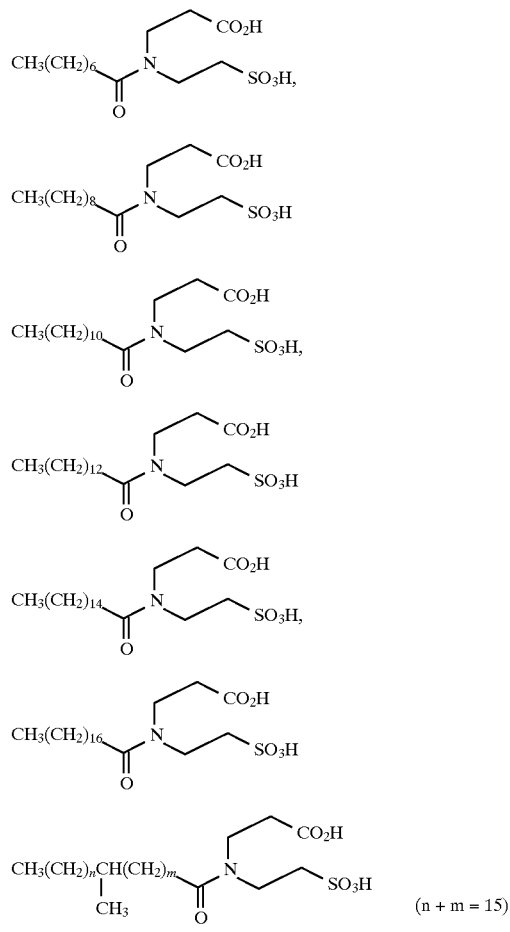

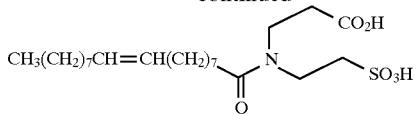

The taurine derivative of the present invention represented by the formula (1) (hereinafter referred to simply as "taurine derivative (1)") can be synthesized via the following synthetic routes.

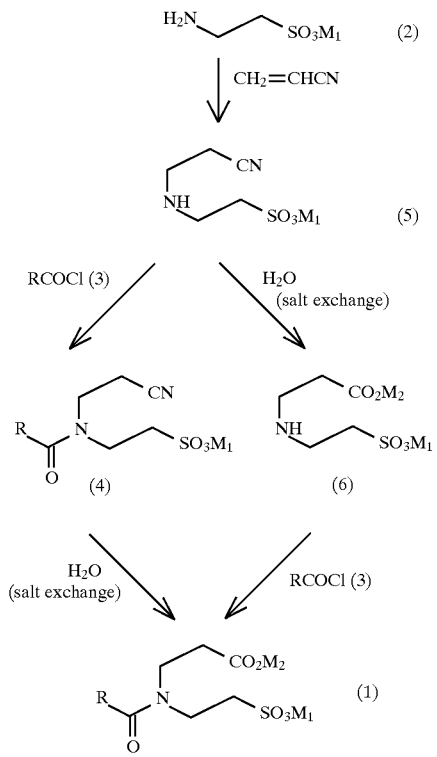

wherein R, $M_1$ and $M_2$ are each as defined above.

The taurine derivative (1) can easily be produced by, for example, the following processes 1 or 2.

(1st process)

Taurine or its salt represented by the formula (2) (hereinafter referred to simply as "taurine or its salt (2)") is reacted with acrylonitrile to thereby give a taurine derivative represented by the formula (5) (hereinafter referred to simply as "taurine derivative (5)"). Then, the taurine derivative (5) is reacted with an acylating agent represented by the formula (7): RCOX (7) (hereinafter referred to simply as "acylating agent (7)") wherein R is as defined above and X represents a chlorine atom, a hydroxyl group, a group represented by the formula: RCOO— (in which R is as defined above) or a group represented by the formula: R'O— (in which R' represents a lower ($C_{1-4}$) alkyl group), preferably with an acid chloride represented by the formula (3) (hereinafter referred to simply as "acid chloride (3)") which ensures a high reaction rate to thereby give a taurine derivative represented by the formula (4) (hereinafter referred to simply as "taurine derivative (4)"). The cyano group of the thus obtained taurine derivative (4) is hydrolyzed, preferably in the presence of an alkali metal hydroxide or an alkaline earth metal hydroxide, optionally followed by salt exchange.

(2nd process)

A taurine derivative (5) is prepared in the same manner as in the 1st process. The cyano group of the thus obtained taurine derivative (5) is hydrolyzed, preferably in the presence of an alkali metal hydroxide or an alkaline earth metal hydroxide, optionally followed by salt exchange, to thereby give a taurine derivative represented by the formula (6) (hereinafter referred to simply as "taurine derivative (6)"). The thus obtained taurine derivative (6) is reacted with an acylating agent (7), preferably an acid chloride (3).

The acid chloride (3) for use in the present invention is not limited as long as it is a compound represented by the formula (3). Examples thereof include hexanoyl chloride, octanoyl chloride, decanoyl chloride, dodecanoyl chloride, tetradecanoyl chloride, hexadecanoyl chloride, octadecanoyl chloride, isostearoyl chloride and oleoyl chloride. Of these, decanoyl chloride, dodecanoyl chloride and tetradecanoyl chloride are preferred. These acid chlorides can easily be produced from the corresponding fatty acids by any of the conventional processes, such as the phosgene process and the phosphorus trichloride process. Although the produced acid chloride may be used as it is, it is distilled before use, depending on the quality demanded.

In the above-mentioned 1st process according to the present invention, 1 equivalent of taurine or its salt (2) is reacted with 0.5 to 10, preferably 0.75 to 5, equivalents of acrylonitrile at an appropriate temperature between 10° and 100° C., preferably between 20° and 75° C., in the presence of water for 1 to 20 hrs, preferably 2 to 10 hrs. Thus, a taurine derivative (5) is obtained. In this reaction, it is preferred that acrylonitrile be gradually added to the reaction system to obtain an improved yield.

Then, 1 equivalent of the resulting taurine derivative (5) is reacted with 0.8 to 1.5, preferably. 0.9 to 1.2, equivalents of an acid chloride (3) at an appropriate temperature between 0° and 100° C., preferably between 10° and 50° C., in the presence of water and, if necessary, a polar solvent such as acetone, methanol, ethanol and isopropanol, for 1 to 20 hrs, preferably 2 to 10 hrs. Thus, a taurine derivative (4) is obtained. In this reaction, generated hydrogen chloride is preferably neutralized with an alkali substance such as sodium hydroxide, potassium hydroxide and aqueous ammonia.

Next, 1 equivalent of the resulting taurine derivative (4) is reacted with preferably 1 to 2 equivalents of an alkali metal hydroxide, such as sodium hydroxide and potassium hydroxide, or an alkaline earth metal hydroxide, such as calcium hydroxide, at an appropriate temperature between 40° and 100° C. in the presence of water and, if necessary, a polar solvent such as acetone, methanol, ethanol and isopropanol, for 1 to 100 hrs, preferably 2 to 50 hrs, while removing generated ammonia, by allowing it to distill from the reaction mixture. This reaction is optionally followed by salt exchange. Thus, a taurine derivative (1) is obtained.

An alkali metal salt and alkaline earth metal salt other than the taurine derivative (1), a fatty acid, an alkanoyltaurine, etc., are contained in the reaction mixture comprising the taurine derivative (1) obtained by the above process. Although the reaction mixture may be used as is, depending on the use, according to necessity, it is subjected to electrodialysis, solvent extraction and/or recrystallization to thereby obtain a highly purified product. An acidic substance such as hydrochloric acid and phosphoric acid may be added to the resulting taurine derivative (1) to adjust the pH value thereof to a desired value.

In the 2nd process according to the present invention, 1 equivalent of the taurine derivative (5) obtained in the same manner as the one described in the above 1st process is reacted with preferably 1 to 2 equivalents of an alkali metal hydroxide, such as sodium hydroxide and potassium hydroxide, or an alkaline earth metal hydroxide, such as calcium hydroxide, at an appropriate temperature between 40° and 100° C. in the presence of water and, if necessary, a polar solvent such as acetone, methanol, ethanol and isopropanol, for 1 to 100 hrs, preferably 2 to 50 hrs. This reaction is optionally followed by salt exchange. Thus, a taurine derivative (6) is obtained. It is preferred that the above reaction be carried out while removing generated ammonia, by allowing it to distill from the reaction mixture.

Then, 1 equivalent of the resulting taurine derivative (6) is reacted with 0.8 to 1.5, preferably 0.9 to 1.2, equivalents of an acid chloride (3) at an appropriate temperature between 0° and 100° C., preferably between 20° and 500° C., in the presence of water and, if necessary, a polar solvent such as acetone, methanol, ethanol and isopropanol, for 1 to 20 hrs, preferably 2 to 10 hrs, while neutralizing generated hydrogen chloride with an alkali substance such as sodium hydroxide, potassium hydroxide and aqueous ammonia. Thus, a taurine derivative (1) is obtained.

The reaction mixture comprising the taurine derivative (1) obtained by the 2nd process may be purified and/or adjusted with respect to pH by the above methods, as in the reaction mixture comprising the taurine derivative (1) obtained by the 1st process.

The taurine derivative (1) of the present invention is a novel compound and exhibits excellent properties as a surfactant for a body cleanser or shampoo, and its irritancy is low. Therefore, the taurine derivative (1) of the present invention is suitable for use in the preparation of a cleanser composition employed for cleansing the body, hair, etc.

Also, the taurine derivatives (4), (5) and (6) of the present invention are novel compounds. These are useful as intermediates for synthesizing the taurine derivative (1). In particular, the taurine derivative (4) itself exhibits excellent properties as a surfactant for a body cleanser or shampoo, and its irritancy is low. Therefore, the taurine derivative (4) of the present invention is suitable for use in the preparation of a cleanser composition employed for cleansing the body, hair, etc.

The cleanser compositions of the present invention contain the taurine derivatives (1) or (4). The amount thereof is preferably 0.5 to 70% by weight, still more preferably 5 to 50% by weight, based on the total weight of the composition. Typically, the compositions will also contain water.

The cleanser compositions of the present invention may contain other conventional components of body and hair cleansers as long as the presence of such components is not detrimental to the effect of the present invention. Examples of the such other components include anionic surfactants such as acyltaurine salts, acylmethyltaurine salts, fatty acid soaps, $C_{8-22}$-alkyl sulfuric acid salts and $C_{8-22}$-alkyl phosphoric acid salts, nonionic surfactants such as polyoxyethylene $C_{8-22}$-alkyl ethers, polyoxypropylene $C_{8-22}$-alkyl ethers, fatty acid diethanolamides, fatty acid monoethanolamides and sorbitan esters, amphoteric surfactants such as lauryl dimethylacetic acid betaine, cationic surfactants, silicone derivatives, water-soluble cationic polymers, humectants, disinfectants, emulsifiers and fragrances.

The present compositions may be used to wash the hair and/or body as well as articles such as tableware. In such methods, a composition according to the present invention is applied to the hair, skin or article for a sufficient time to effect cleaning of the hair, skin or article, and then rinsed from the hair, skin or article with water. Although it is preferred that the hair or skin be human, the present compositions may also be used to wash the hair or skin of animals such as cats, dogs, etc.

Namely, the present invention includes a method of washing hair or skin which comprises contacting said hair or skin with the above-mentioned composition of the present invention, in other words, a method of washing hair or skin which comprises using the above-mentioned taurine derivative (1) or (4) of the present invention.

Other features of the invention will become apparent in the course of the following descriptions of exemplary embodiments which are given for illustration of the invenition and are not intended to be limiting thereof.

EXAMPLES

Unless otherwise specified, all percentages given in the following examples are wt. %.

Example 1
Potassium salt of cyanoetbyltaurine 500 ml of deionized water was put in a 2 l round bottom flask equipped with a stirrer, a dropping funnel and a thermometer. 250.0 g (2.0 mol) of taurine and 112.2 g (2.0 mol) of potassium hydroxide were added thereto and dissolved. The temperature of the contents in the flask was raised to about 50° C., and then 106.0 g (2.0 mol) of acrylonitrile was dropwise added thereto over a period of about 1 hr while stirring. During the dropwise addition, the temperature of the contents rose due to an exothermic reaction, but the temperature was maintained at about 60° C. until the completion of the dropwise addition. After the completion of the dropwise addition, the stirring of the reaction mixtre was continued at 60° C. for 1 hr. Thereafter, the solvent was removed by distillation under a reduced pressure to thereby obtain a residue (white solid). The residue was dried in a desiccator. Thus, 408.5 g of the potassium salt of cyanoethyltaurine was obtained (yield: 99.1%). The infrared absorption spectrum thereof was as follows:
Infrared absorption spectrum (KBr pellet method)
3100–2000 (N—H stretching vibration),
2254 (C≡N stretching vibration),
1190, 1055 (S=O stretching vibration) cm$^{-1}$

Example 2
Potassium salt of N-lauroyl-N-cyanoethyltaurine 405.5 g (1.98 mol) of the potassium salt of cyanoethyltaurine synthesized in Example 1 was dissolved in 2 l of deionized water. The resulting aqueous solution was put in a 5 l round bottom flask equipped with a stirrer, a dropping funnel and a thermometer, and then 437.5 g (2.0 mol) of lauroyl chloride was dropwise added to the aqueous solution over a period of about 2 hrs under stirring. During the dropwise addition, hydrogen chloride was generated as a by-product in accordance with the progress of the reaction to thereby lower the pH value of the reaction system. Therefore, a 20% aqueous potassium hydroxide solution was added thereto together with the lauroyl chloride to thereby maintain the pH of the reaction system on the alkaline side. The reaction system was maintained at a temperature of 20° to 30° C. during the dropwise addition of the lauroyl chloride and aqueous potassium hydroxide solution. The viscosity of the reaction system increased during the dropwise addition of the lauroyl chloride and aqueous potassium hydroxide solution, so that 1 l of deionized water and 500 ml of acetone were fed into the reaction system as solvents. After the completion of the dropwise addition, the stirring of the reaction mixture was continued at 25° C. for about 2 hrs. Thereafter, the solvent was removed by distillation under a reduced pressure to thereby obtain 774.9 g of the potassium salt of N-lauroyl-N-cyanoethyltaurine (yield: 98.0%). The infrared absorption spectrum thereof was as follows:
Infrared absorption spectrum (KBr pellet method)
2926, 2860 (C—H stretching vibration),
2254 (C≡N stretching vibration),
1632 (C=O stretching vibration),
1191, 1047 (S=O stretching vibration) cm$^{-1}$

Example 3
Potassium salt of N-lauroyl-N-coarboxyetyltaurine

About 3 l of deionized water was put in a 5 l round bottom flask equipped with a stirrer, a dropping funnel and a thermometer. 770 g (1.93 mol) of the potassium salt of N-lauroyl-N-cyanoethyltaurine synthesized in Example 2 and 134.7 g (2.4 mol) of potassium hydroxide were added thereto and dissolved. The temperature of the aqueous solution was raised to 95° C., and the stirring thereof was continued for about 15 hrs under a nitrogen stream while removing generated ammonia gas to thereby effect the reaction. After the completion of the reaction, the contents in the flask were cooled to room temperature, and then a 5% aqueous hydrochloric acid solution was added thereto to thereby adjust the pH of the contents to 2. The resulting mixture was allowed to stand still at room temperature for about 1 hr, and the white crystals which precipitated were recovered by filtration. The crystals thus obtained were dissolved in hot ethanol to effect recrystallization. The resulting white crystals were dried under a reduced pressure to thereby obtain 628.9 g of the monopotassium salt of N-lauroyl-N-carboxyethyltaurine (isolated yield: 78.0%). The infrared absorption spectrum thereof, the $^1$H-NMR spectrum thereof and the result of elemental analysis thereof were as follows.
Infrared absorption spectrum (KBr pellet method)
2926, 2860 (C—H stretching vibration),
1728, 1617 (C=O stretching vibration),
1194, 1056 (S=O stretching vibration) cm$^{-1}$
$^1$H-NMR spectrum (in D$_2$O)

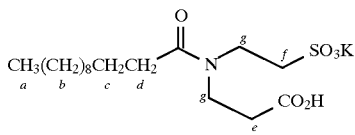

a: 0.60 ppm(t,3H), b: 1.02 ppm(m,16H),
c: 1.32 ppm(m,2H), d: 2.12 ppm(t,2H),
e: 2.41 ppm(t,2H), f: 2.87 ppm(t,2H),
g: 3.41 ppm(m,4H)
Elemental analysis (C$_{17}$H$_{32}$O$_6$NSK=417.59)
Calculated(%) C 48.90, H 7.72, O 22.99, N 3.35
Found(%) C 48.79, H 7.73, O 23.05, N 3.34

Example 4
Disodium salt of N-carboxyethyltaurine 300 ml of deionized water was put in a 3 l round bottom flask equipped with a stirrer, a dropping funnel and a thermometer. 125.0 g (1.0 mol) of taurine and 40.0 g (1.0 mol) of sodium hydroxide were added thereto and dissolved. The temperature of the contents in the flask was raised to about 50° C., and then 53.0 g (1.0 mol) of acrylonitrile was dropwise added thereto over a period of about 1 hr while stirring. During the dropwise addition, the temperature of the contents rose due to an exothermic reaction, but the temperature was maintained at about 60° C. until the completion of the dropwise addition. After the completion of the dropwise addition, the stirring of the reaction mixture was continued at 60° C. for 1 hr to complete the reaction and aging. After the completion of the reaction and aging, 60.0 g (1.5 mol) of sodium hydroxide was added to the reaction mixture with stirring. Then, the resulting mixture was stirred at 95° C. for 5 hrs. Nitrogen was introduced into the flask, and the ammonia gas generated during the stirring was removed. The solvent was removed from the reaction mixture by distillation under a reduced pressure to thereby obtain 240.5 g of the disodium salt of N-carboxyethyltaurine (yield: 99.8%). The infrared absorption spectrum thereof was as follows:

Infrared absorption spectrum (KBr pellet method)

3100–2000 (N—H stretching vibration),
1580, 1405 (C=O stretching vibration),
1190, 1055 (S=O stretching vibration) cm$^{-1}$ Example 5

Sodium salt of N-lauroyl-N-carboxyethyltaurine 1 l of deionized water was put in a 3 l round bottom flask equipped with a stirrer, a dropping funnel and a thermometer. 240.0 g (1.0 mol) of the disodium salt of N-carboxyethyltaurine synthesized in Example 4 was added thereto and dissolved. 218.8 g (1.0 mol) of lauroyl chloride was dropwise added to the obtained aqueous solution over a period of about 2 hrs while stirring. During the dropwise addition, hydrogen chloride was generated as a by-product in accordance with the progress of the reaction to thereby lower the pH value of the reaction system. Therefore, a 20% aqueous sodium hydroxide solution was dropwise added thereto together with the lauroyl chloride to thereby maintain the pH of the reaction system on the alkaline side. The reaction system was maintained at a temperature of 20° to 30° C. during the dropwise addition of the lauroyl chloride and aqueous sodium hydroxide solution. The viscosity of the reaction system increased during the dropwise addition of the lauroyl chloride and aqueous potassium hydroxide solution, so that 300 ml of deionized water and 150 ml of acetone were fed into the reaction system as solvents. After the completion of the dropwise addition, the stirring of the resultant mixture was continued at 25° C. for about 2 hrs to complete the reaction. After the completion of the reaction, a 5% aqueous hydrochloric acid solution was added thereto to adjust the pH of the mixture to 2. The resulting mixture was allowed to stand still at room temperature for about 1 hr, and the white crystals which precipitated were recovered by filtration. The resulting crystals were dissolved in hot ethanol to effect recrystallization. The white crystals thus obtained were dried under a reduced pressure to thereby obtain 345.3 g of the monosodium salt of N-lauroyl-N-carboxyethyltaurine (isolated yield: 86.0%). The infrared absorption spectrum thereof, the $^1$H-NMR spectrum thereof and the result of the elemental analysis thereof were as follows:

Infrared absorption spectrum (KBr pellet method)

2926, 2854 (C—H stretching vibration),
1731, 1611 (C=O stretching vibration),
1203, 1059 (S=O stretching vibration) cm$^{-1}$ $^1$H-NMR spectrum (in D$_2$O)

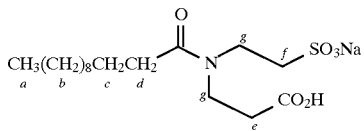

a: 0.61 ppm(t,3H), b: 1.02 ppm(m,16H),
c: 1.30 ppm(m,2H), d: 2.10 ppm(t,2H),
e: 2.39 ppm(t,2H), f: 2.87 ppm(t,2H),
g: 3.40 ppm(m,4H)

Elemental analysis (C$_{17}$H$_{32}$O$_6$NSNa=401.48)
Calculated(%) C 50.86, H 8.03, O 23.91, N 3.49
Found(%) C 50.90, H 7.99, O 23.68, N 3.50

Example 6

Sodium salt of N-decanoyl-N-carboxyethyltaurine 503.8 g (1.15 mol) of a 45.7% aqueous solution of the sodium salt of cyanoethyltaurine was put in a 2 l round bottom flask equipped with a stirrer, a dropping funnel and a thermometer. 220.4 g (1.16 mol) of decanoyl chloride was dropwise added thereto over a period of about 2 hrs while stirring. During the dropwise addition, hydrogen chloride was generated as a by-product in accordance with the progress of the reaction to thereby lower the pH value of the reaction system. Therefore, a 20% aqueous sodium hydroxide solution was dropwise added thereto together with the decanoyl chloride to thereby maintain the pH of the reaction system on the alkaline side (pH 9 to 11). The reaction system was maintained at a temperature of 20° to 30° C. during the dropwise addition of the decanoyl chloride and aqueous sodium hydroxide solution. The viscosity of the reaction system increased during the dropwise addition of the decanoyl chloride and aqueous potassium hydroxide solution, so that 100 ml of acetone was fed into the reaction system as a solvent. After the completion of the dropwise addition, the stirring of the resultant mixture was continued at 25° C. for about 2 hrs. Subsequently, the hydrolysis of the cyano group was carried out. Namely, 69.0 g (1.73 mol) of sodium hydroxide was added to the obtained reaction mixture, and the temperature of the resulting mixture was raised while distilling off acetone. After the temperature of the mixture reached 95° C., the stirring of the mixture was continued for about 3 hrs under a nitrogen stream while removing generated ammonia gas to thereby effect a reaction. After the completion of the reaction, the reaction mixture was cooled to room temperature, and then a 5% aqueous hydrochloric acid solution was added thereto to adjust the pH of the mixture to 1. The resulting mixture was allowed to stand still at room temperature for about 1 hr, and the white crystals which precipitated were recovered by filtration, The resulting crystals were dissolved in hot ethanol to effect recrystallization. The white crystals thus obtained were dried under a reduced pressure to thereby obtain 409.6 g of the monosodium salt of N-decanoyl-N-carboxyethyltaurine (isolated yield: 95.4%). The infrared absorption spectrum thereof, the $^1$H-NMR spectrum thereof and the result of the elemental analysis thereof were as follows:

Infrared absorption spectrum (KRr tablet method)

2926, 2860 (C—H stretching vibration),
1730, 1615 (C=O stretching vibration), 1198, 1057 (S=O stretching vibration) cm$^{-1}$
$^1$H-NMR spectrum (in $D_2O$)

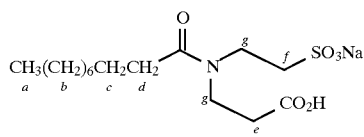

a: 0.65 ppm(t,3H), b: 1.10 ppm(m,12H),
c: 1.30 ppm(m,2H), d: 2.15 ppm(t,2H),
e: 2.43 ppm(t,2H), f: 2.90 ppm(t,2H),
g: 3.43 ppm(m,4H)
Elemental analysis ($C_{15}H_{28}O_6NSNa$=373.41)
Calculated(%) C 48.25, H 7.55, O 25.71, N 3.75
Found(%) C 48.40, H 7.61, O 25.63, N 3.79

Example 7

Ammonium salt of N-lauroyl-N-carboxyethyltaurine 100 g (0.25 mol) of sodium salt of the N-lauroyl-N-carboxyethyltaurine synthesized in Example 5 was dissolved in 500 ml of deionized water. The aqueous solution thus obtained was placed in an electrodialysis ion exchanger (Microacylizer EX3, bench desalter manufactured by Asahi Chemical Co., Ltd.), thereby exchanging the counter ion of the sodium salt of N-lauroyl-N-carboxyethyltaurine for ammonium ion. Specifically, electrodialysis was conducted for 5 hrs while charging 1 l of 1N sulfuric acid into the aqueous solution of sodium salt of N-lauroyl-N-carboxyethyltaurine by the use of a microtube pump over a period of about 3 hrs. After the completion of the electrodialysis, the resulting aqueous solution was neutralized with 10% aqueous ammonia, thereby adjusting the pH of the solution to 7. The amount of the anionic surfactant contained in the obtained aqueous solution was measured by the Epton method, thereby finding that it was 15.3%. The measurement of the Na content thereof showed that it was 0.01% or below.

Test Example 1

The foaming power of each of the taurine derivatives and the comparative compound specified in Table 1 was measured by the following method. The results are shown in Table 1.

<Foaming power test>

0.3% by weight of lanolin and 0.1% by weight of a surfactant were added to 4° DH hard water at 40° C., and the mixture thus obtained was stirred for 30 sec according to the reverse stirring method. The volume of the foam was measured 10 sec and 120 sec after the the stirring was stopped.

TABLE 1

| | | Volume of foam | |
|---|---|---|---|
| Surfactant | | after 10 sec | after 120 sec |
| $CH_3(CH_2)_{10}$–CO–N(CH$_2$CH$_2$SO$_3$Na)(CH$_2$CH$_2$CO$_2$H) (Ex. 5) | | 190 | 183 |

TABLE 1-continued

| | | Volume of foam | |
|---|---|---|---|
| Surfactant | | after 10 sec | after 120 sec |
| $CH_3(CH_2)_8$–CO–N(CH$_2$CH$_2$SO$_3$Na)(CH$_2$CH$_2$CO$_2$H) (Ex. 6) | | 175 | 165 |
| $CH_3(CH_2)_{10}$–CO–N(CH$_2$CH$_2$SO$_3$K)(CH$_2$CH$_2$CN) (Ex. 2) | | 205 | 185 |
| $CH_3(CH_2)_{11}O(CH_2CH_2O)_{8.0}$–SO$_3$Na | (Comp. cpd.) | 170 | 90 |

Test Example 2

With respect to each of the taurine derivatives of the present invention and the comparative compound specified in Table 2, the irritation of the skin was evaluated by the following four-cumulative-stimuli testing method. The results are also shown in Table 2.

<Four-cumulative-stimuli testing method>

An aqueous solution containing 10% by weight of each of the surfactants was applied to the healthy skin of each of five guinea pigs four times. The reaction of the skin after the fourth application of the solution was evaluated according to the following criteria. The average values in the evaluation are shown in Table 2.

<Evaluation criteria>

0: no reaction observed;
1: slight erythema observed;
2: clear erythema observed;
3: clear erythema accompanied with edema; and
4: clear erythema accompanied with necrosis or asphyxia.

TABLE 2

| Surfactant | | Av. value in the evaluation |
|---|---|---|
| $CH_3(CH_2)_{10}$–CO–N(CH$_2$CH$_2$SO$_3$Na)(CH$_2$CH$_2$CO$_2$H) | (Ex. 5) | 0.4 |
| $CH_3(CH_2)_8$–CO–N(CH$_2$CH$_2$SO$_3$Na)(CH$_2$CH$_2$CO$_2$H) | (Ex. 6) | 0.2 |
| $C_{12}H_{25}O$–SO$_3$Na | (Comp. cpd.) | 2.6 |

Formulation Example 1

A shampoo having the following formulation was prepared. The obtained shampoo not only was excellent in foaming power and detergency, but also ensured a good feeling in washing and rinsing the hair.

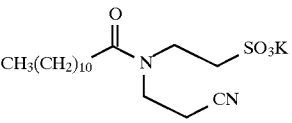

| | |
|---|---|
| | 15% by weight |
| lauroyldiethanolamide | 3% by weight |
| lauryldimethylamine oxide | 0.5% by weight |
| hydroxyethylcellulose (SE-850K produced by Daicel Chemical Industries, Ltd.) | 0.1% by weight |
| sodium benzoate | appropriate amount |
| coloring matter | appropriate amount |
| fragrance | appropriate amount |
| NaOH | appropriate amount |
| water | q.s. ad 100 |
| pH 6.5 | |

Formulation Example 2

A shampoo having the following formulation was prepared. The obtained shampoo not only was excellent in foaming power and detergency, but also ensured a good feeling in washing and rinsing the hair.

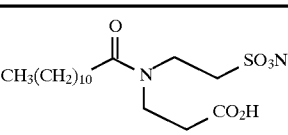

| | |
|---|---|
| | 15% by weight |
| lauroyldiethanolamide | 3% by weight |
| lauryl dimethylacetic acid betaine | 0.5% by weight |
| hydroxyethylcellulose (SE-850K produced by Daicel Chemical Industries, Ltd.) | 0.1% by weight |
| sodium benzoate | appropriate amount |
| coloring matter | appropriate amount |
| fragrance | appropriate amount |
| NaOH | appropriate amount |
| water | q.s. ad 100 |
| pH 6.5 | |

Formulation Example 3

A body shampoo having the following formulation was prepared. The obtained body shampoo was excellent in foaming power and detergency, could be quickly rinsed, and ensured a refreshing and good feeling both during rinsing and after washing.

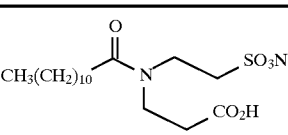

| | |
|---|---|
| | 15% by weight |
| lauryl dimethylacetic acid betaine | 3% by weight |
| lauric acid | 0.5% by weight |
| sucrose fatty acid ester | 0.1% by weight |
| methyl paraben | appropriate amount |
| coloring matter | appropriate amount |
| fragrance | appropriate amount |
| NaOH | appropriate amount |
| water | q.s. ad 100 |
| pH 6.0 | |

Formulation Example 4

A body shampoo having the following formulation was prepared. The obtained body shampoo was excellent in foaming power and detergency, could be quickly rinsed, and ensured a refreshing and good feeling both during rinsing and after washing.

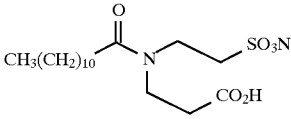

| | |
|---|---|
| | 15% by weight |
| triethanolamine salt of lauric acid | 3% by weight |
| sucrose fatty acid ester | 0.5% by weight |
| lauryldimethylamine oxide | 0.1% by weight |
| methyl paraben | appropriate amount |
| coloring matter | appropriate amount |
| fragrance | appropriate amount |
| NaOH | appropriate amount |
| water | q.s. ad 100 |
| pH 7.0 | |

This application is based on Japanese Patent Application No. 6-24443, filed Feb. 22, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

We claim:

1. A taurine derivative represented by the following formula (1):

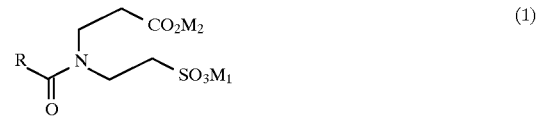

(1)

wherein R is a linear or branched alkyl or alkenyl group having 5 to 21 carbon atoms, and $M_1$ and $M_2$ are the same or different from each other and each independently is a hydrogen atom, an alkali metal atom, ½ (an alkaline earth metal atom), an ammonium group, a mono-, di-, tri- or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid.

2. The taurine derivative of claim 1, wherein R is a linear or branched alkyl or alkenyl group having 7 to 19 carbon atoms, and $M_1$ and $M_2$ are the same or different from each other and each independently is a hydrogen atom, a sodium atom, a potassium atom, an ammonium group, a triethenolammonium group, a diethanolammonium group or a monoethanolammonium group.

3. The taurine derivative of claim 1, wherein R is a linear or branched alkyl or alkenyl group having 9 to 13 carbon atoms, and $M_1$ and $M_2$ are the same or different from each other and each independently is a hydrogen atom, a sodium atom, a potassium atom or an ammonium group.

4. A process for producing a taurine derivative represented by the following formula (1):

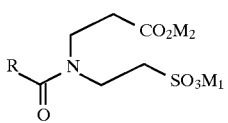
(1)

wherein R is a linear or branched alkyl or alkenyl group having 5 to 21 carbon atoms, and $M_1$ and $M_2$ are the same or different from each other and each independently is a hydrogen atom, an alkali metal atom, ½ (an alkaline earth metal atom), an ammonium group, a mono-, di-, tri- or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid, which comprises hydrolyzing the cyano group of a taurine derivative represented by the following formula (4), optionally followed by salt exchange:

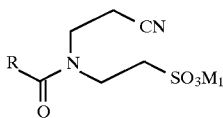
(4)

wherein R and $M_1$ are each as defined above.

5. The process of claim 4, wherein the hydrolysis is performed in the presence of an alkali metal hydroxide or an alkaline earth metal hydroxide.

6. A cleanser composition, comprising a taurine derivative represented by the following formula (1):

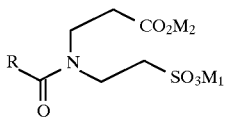
(1)

wherein R is a linear or branched alkyl or alkenyl group having 5 to 21 carbon atoms, and $M_1$ and $M_2$ are the same or different from each other and each independently is a hydrogen atom, an alkali metal atom, ½ (an alkaline earth metal atom), an ammonium group, a mono-, di-, tri- or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid.

7. The cleanser composition of claim 6, which contains the taurine derivative in an amount of 0.5 to 70% by weight, based on the total weight of the composition.

8. A taurine derivative represented by the following formula (4):

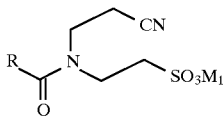
(4)

wherein R is a linear or branched alkyl or alkenyl group having 5 to 21 carbon atoms, and $M_1$ is a hydrogen atom, an alkali metal atom, ½ (an alkaline earth metal atom), an ammonium group, a mono-, di-, tri- or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid.

9. The taurine derivative of claim 8, wherein R is a linear or branched alkyl or alkenyl group having 9 to 13 carbon atoms, and $M_1$ is a hydrogen atom, a sodium atom, a potassium atom or an ammonium group.

10. A process for producing a taurine derivative represented by the following formula (4):

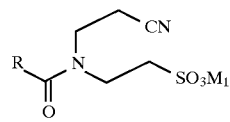
(4)

wherein R is a linear or branched alkyl or alkenyl group having 5 to 21 carbon atoms, and $M_1$ is a hydrogen atom, an alkali metal atom, ½ (an alkaline earth metal atom), an ammonium group, a mono-, di-, tri- or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid, which comprises reacting a taurine derivative represented by the following formula (5):

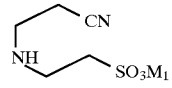
(5)

wherein $M_1$ is as defined above, with an acid chloride represented by the following formula (3):

RCOCl (3)

wherein R is as defined above.

11. A cleanser composition comprising a taurine derivative represented by the following formula (4):

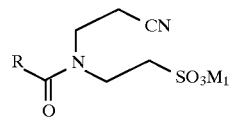
(4)

wherein R is a linear or branched alkyl or alkenyl group having 5 to 21 carbon atoms, and $M_1$ is a hydrogen atom, an alkali metal atom, ½ (an alkaline earth metal atom), an ammonium group, a mono-, di-, tri- or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid.

12. The cleanser composition of claim 11, which contains the taurine derivative in an amount of 0.5 to 70% by weight, based on the total weight of the composition.

13. A method of washing hair or skin which comprises contacting said hair or skin with a composition comprising a taurine derivative represented by the following formula (1):

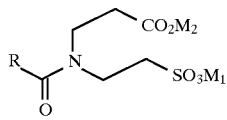 (1)

wherein R is a linear or branched alkyl or alkenyl group having 5 to 21 carbon atoms, and $M_1$ and $M_2$ are the same or different from each other and each independently is a hydrogen atom, an alkali metal atom, ½ (an alkaline earth metal atom), an ammonium group, a mono-, di-, tri- or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid.

14. A method of washing hair or skin which comprises contacting said hair or skin with a composition comprising a taurine derivative represented by the following formula (4):

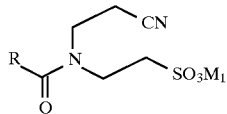 (4)

wherein R is a linear or branched alkyl or alkenyl group having 5 to 21 carbon atoms, and $M_1$ is a hydrogen atom, an alkali metal atom, ½ (an alkaline earth metal atom), an ammonium group, a mono-, di-, tri- or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid.

15. A method of washing hair or skin which comprises using a taurine derivative represented by the following formula (1):

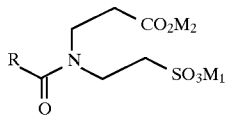 (1)

wherein R is a liner or branched alkyl or alkenyl group having 5 to 21 carbon atoms, and $M_1$ and $M_2$ are the same or different from each other and each independently is a hydrogen atom, an alkali metal atom, ½ (an alkaline earth metal atom), an ammonium group, a mono-, di-, tri-, or tetraalkylammonium group having 1 to 22 carbon atoms in total, a mono-, di-, tri- or tetraalkenylammonium group having 2 to 22 carbon atoms in total, a mono-, di-, tri- or tetraalkanolammonium group having 2 to 8 carbon atoms in total, an N-alkylpyridinium group having 1 to 18 carbon atoms in the N-alkyl group, an N-alkenylpyridinium group having 2 to 18 carbon atoms in the N-alkenyl group or a protonated basic amino acid.

* * * * *